United States Patent
Lee

(10) Patent No.: US 9,510,776 B2
(45) Date of Patent: Dec. 6, 2016

(54) SHOE INSOLE SENSOR FOR WALK DIAGNOSIS AND SHOE INSOLE FLEXIBLE BOARD COMBINED WITH THE SAME

(71) Applicant: Jin-Wook Lee, Seoul (KR)

(72) Inventor: Jin-Wook Lee, Seoul (KR)

( * ) Notice: Subject to any disclaimer, the term of this patent is extended or adjusted under 35 U.S.C. 154(b) by 0 days.

(21) Appl. No.: 14/360,493

(22) PCT Filed: Nov. 15, 2012

(86) PCT No.: PCT/KR2012/009669
§ 371 (c)(1),
(2) Date: May 23, 2014

(87) PCT Pub. No.: WO2013/081320
PCT Pub. Date: Jun. 6, 2013

(65) Prior Publication Data
US 2014/0326085 A1 Nov. 6, 2014

(30) Foreign Application Priority Data
Nov. 29, 2011 (KR) .......................... 10-2011-0125516

(51) Int. Cl.
*A61B 5/103* (2006.01)
*A61B 5/11* (2006.01)
(Continued)

(52) U.S. Cl.
CPC ............ *A61B 5/1116* (2013.01); *A43B 3/0005* (2013.01); *A61B 5/1036* (2013.01); *A61B 5/112* (2013.01); *A61B 5/6807* (2013.01); *A61B 5/6829* (2013.01)

(58) Field of Classification Search
None
See application file for complete search history.

(56) References Cited

U.S. PATENT DOCUMENTS 4,029,386 A * 6/1977 Krantz, Jr. ......... H01R 13/7197
333/182
6,152,303 A * 11/2000 Ducote ................. H01M 2/105
206/446
(Continued)

FOREIGN PATENT DOCUMENTS

KR 10-0702613 B1 3/2007
KR 20110124964 A 11/2011

OTHER PUBLICATIONS

International Search Report issued Mar. 20, 2013 in PCT/KR2012/009669 filed on Nov. 15, 2012.
(Continued)

*Primary Examiner* — Robert R Raevis
(74) *Attorney, Agent, or Firm* — Harness, Dickey & Pierce, P.L.C.

(57) ABSTRACT

A shoe insole sensor includes a body including a plurality of recessed regions formed at respective locations corresponding to vertexes of N-polygon, where N is an even number, a plurality of first protrusions formed in odd recessed regions of the recessed regions, where each of the first protrusions has a first height, and a plurality of second protrusions formed in even recessed regions of the recessed regions, where each of the second protrusions has a second height different from the first height. Here, the body is formed with a nonconductive material, each of the first protrusions is formed with a conductive material, and each of the second protrusions is formed with a conductive material.

4 Claims, 11 Drawing Sheets

(51) Int. Cl.
*A61B 5/00* (2006.01)
*A43B 3/00* (2006.01)

(56) References Cited

U.S. PATENT DOCUMENTS

| | | |
|---|---|---|
| 6,807,869 B2 | 10/2004 | Farringdon et al. |
| 2003/0097878 A1 | 5/2003 | Farringdon et al. |
| 2004/0192092 A1* | 9/2004 | Borrego Bel .......... H01R 13/53 439/181 |
| 2004/0214470 A1* | 10/2004 | Hori ................... H01R 13/6275 439/489 |
| 2008/0203144 A1 | 8/2008 | Kim |
| 2010/0201650 A1 | 8/2010 | Son |

OTHER PUBLICATIONS

Written Opinion issued Mar. 20, 2013 in PCT/KR2012/009669 filed on Nov. 15, 2012.

* cited by examiner though # US 9,510,776 B2

SHOE INSOLE SENSOR FOR WALK DIAGNOSIS AND SHOE INSOLE FLEXIBLE BOARD COMBINED WITH THE SAME

CROSS-REFERENCE TO RELATED APPLICATION(S)

This application is a national phase under 35 U.S.C. §371 of PCT International Application No. PCT/KR2012/009669 which has an International filing date of Nov. 15, 2012, which designated the Republic of Korea and which claims priority to Korean patent application number KR 10-2011-0125516 filed Nov.29, 2011.

BACKGROUND

1. Technical Field

Example embodiments relate generally to a shoe insole for walk diagnosis. More particularly, embodiments of the present inventive concept relate to a shoe insole sensor and a shoe insole flexible board that are included in a shoe insole for walk diagnosis.

2. Description of the Related Art

Generally, walking posture of a person (i.e., walker) includes a lot of information related to his health. Thus, if walking data on which the walking posture of the person can be analyzed is obtained, an individual customized service related to his health may be provided to the person. For this reason, many technologies that use a shoe insole sensor attached to a shoe insole have been suggested to analyze walking posture of a person by extracting walking data of the person.

However, conventional technologies for analyzing the walking posture of the person cost high because the conventional technologies use expensive shoe insole sensors that consume high power. This is because the conventional technologies mostly focus on high performance (e.g., high data resolution, etc). As a result, extracting the walking data has been performed in a specific facility such as a hospital, a health examination center, etc.

Thus, it is difficult to accurately analyze the walking posture of the person based on the walking data extracted during a limited time in a specific facility. That is, in order to accurately analyze walking posture of a person, it is necessary to extract walking data during a long time in real life of the person. Thus, a shoe insole may be required to consume low power, to have a small size, and to be manufactured at low cost.

SUMMARY

Some example embodiments provide a shoe insole sensor capable of providing high data resolution when being combined with a shoe insole flexible board, where the shoe insole sensor combined with the shoe insole flexible board consumes low power, has a small size, and is manufactured at low cost.

Some example embodiments provide a shoe insole flexible board capable of providing high data resolution when being combined with the shoe insole sensor, where the shoe insole flexible board combined with the shoe insole sensor consumes low power, has a small size, and is manufactured at low cost.

According to an aspect of example embodiments, a shoe insole sensor may include a body including a plurality of recessed regions formed at locations corresponding to vertexes of N-polygon, where N is an even number, the body being formed with a nonconductive material, a plurality of first protrusions formed in odd recessed regions of the recessed regions, each of the first protrusions having a first height, each of the first protrusions being formed with a conductive material, and a plurality of second protrusions formed in even recessed regions of the recessed regions, each of the second protrusions having a second height different from the first height, each of the second protrusions being formed with a conductive material.

In example embodiments, the first protrusions and the second protrusions that are adjacent to each other may act as respective sensing pairs, and the sensing pairs may implement data resolution based on the first height and the second height.

In example embodiments, the body may have a cylinder shape.

In example embodiments, each of the recessed regions may have a cylinder shape, each of the first protrusions may have the cylinder shape, and each of the second protrusions may have the cylinder shape.

In example embodiments, the conductive material may include conductive rubber and the nonconductive material may include nonconductive rubber.

In example embodiments, the body may further include at least one concave region for adjusting sensing sensitivity of the shoe insole sensor. In addition, an area of each of the first protrusions and an area of each of the second protrusions may be smaller than an area of each of the recessed regions.

In example embodiments, the sensing sensitivity may be determined based on at least one of a property of the nonconductive rubber, a property of the conductive rubber, the first height of the first protrusions, the second height of the second protrusions, and an entire volume of the concave region.

According to an aspect of example embodiments, a shoe insole flexible board may include a plurality of switching units and a plurality of wiring units connected to the switching units, respectively. Here, each of the switching units may include N switches at locations corresponding to vertexes of N-polygon, where N is an even number, and adjacent two switches of the N switches may act as a sensing pair. In addition, each of wiring units may include a voltage supply line that provides a reference voltage, a first wiring that transfers a first sensing signal, and a second wiring that transfers a second sensing signal.

In example embodiments, the voltage supply line may be connected to the N switches, the first wiring may be connected to first switches of the N switches, and the second wiring may be connected to second switches of the N switches.

In example embodiments, the first sensing signal may be generated when the reference voltage is applied to the first wiring as at least one of the first switches is turned-on.

In example embodiments, the second sensing signal may be generated when the reference voltage is applied to the second wiring as at least one of the second switches is turned-on.

In example embodiments, data resolution may be determined based on whether the first sensing signal is generated and whether the second sensing signal is generated.

In example embodiments, only one of the first sensing signal and the second sensing signal may be generated when a relatively weak pressure is applied.

In example embodiments, both the first sensing signal and the second sensing signal may be generated when a relatively strong pressure is applied.

Therefore, a shoe insole sensor according to example embodiments may provide high data resolution when being combined with a shoe insole flexible board because the shoe insole sensor can accurately detect a pressure using a plurality of protrusions that act as respective sensing pairs when the pressure is applied to the shoe insole sensor in various directions. Here, the shoe insole sensor may consume low power, may have a small size, and may be manufactured at low cost.

in addition, a shoe insole flexible board according to example embodiments may provide high data resolution when being combined with a shoe insole sensor because the shoe insole flexible board can accurately detect a pressure using a plurality of switches that act as respective sensing pairs when the pressure is applied to the shoe insole flexible board in various directions. Here, the shoe insole flexible board may consume low power, may have a small size, and may be manufactured at low cost.

BRIEF DESCRIPTION OF THE DRAWINGS

Illustrative, non-limiting example embodiments will be more clearly understood from the following detailed description taken in conjunction with the accompanying drawings.

DETAILED DESCRIPTION OF THE EMBODIMENTS

Figure 1A:
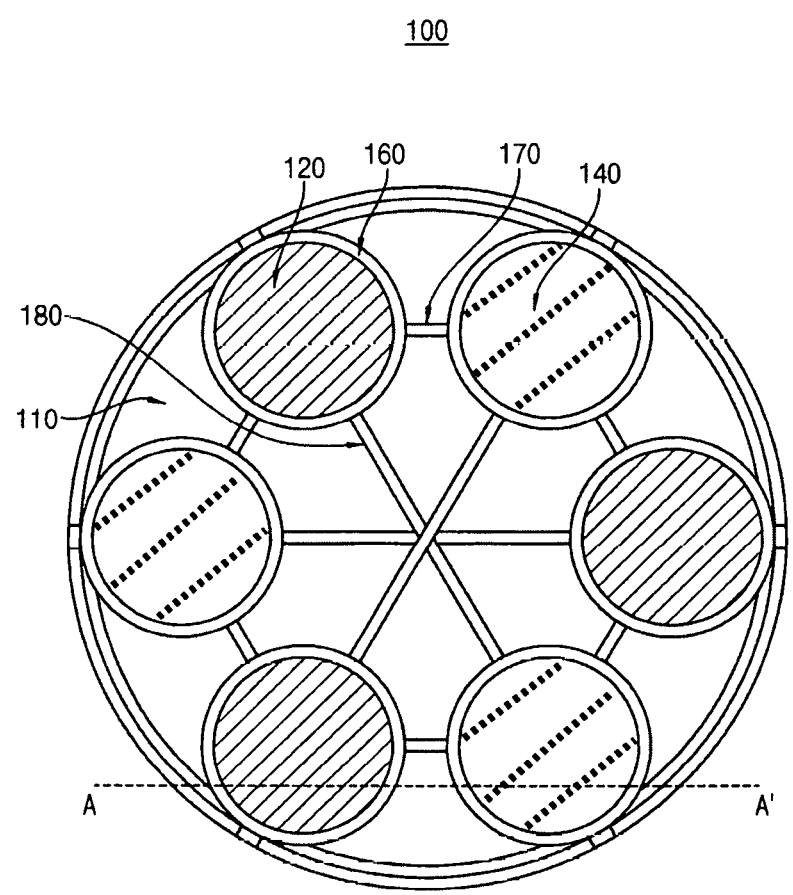
FIGS. 1A and 1B are diagrams illustrating a shoe insole sensor according to example embodiments.

Various example embodiments will be described more fully hereinafter with reference to the accompanying drawings, in which some example embodiments are shown. The present inventive concept may, however, be embodied in many different forms and should not be construed as limited to the example embodiments set forth herein. Rather, these example embodiments are provided so that this disclosure will be thorough and complete, and will fully convey the scope of the present inventive concept to those skilled in the art. In the drawings, the sizes and relative sizes of layers and regions may be exaggerated for clarity. Like numerals refer to like elements throughout.

It will be understood that, although the terms first, second, third etc. may be used herein to describe various elements, these elements should not be limited by these terms. These terms are used to distinguish one element from another. Thus, a first element discussed below could be termed a second element without departing from the teachings of the present inventive concept. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular example embodiments only and is not intended to be limiting of the present inventive concept. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1B:
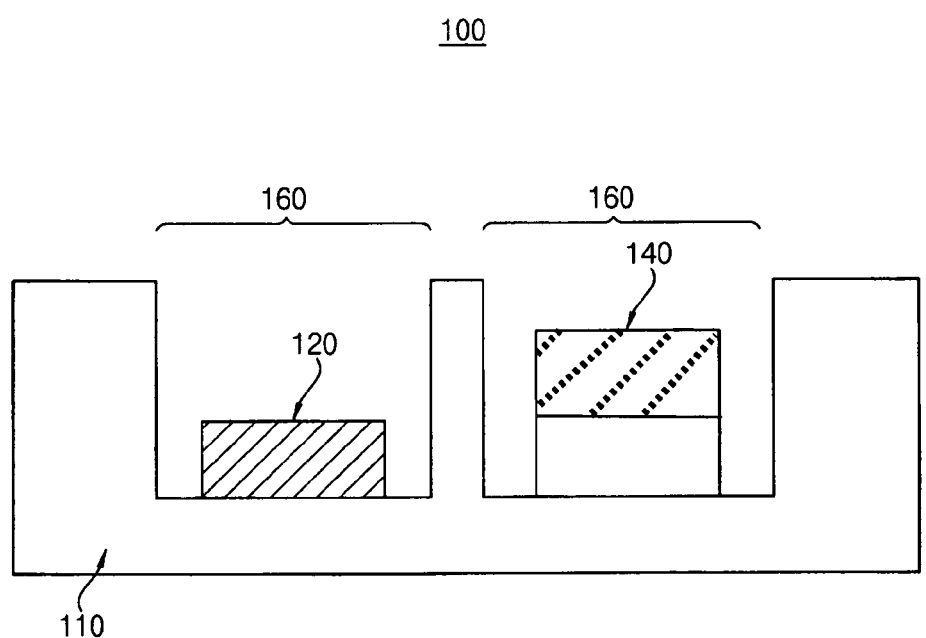

FIGS. 1A and 1B are diagrams illustrating a shoe insole sensor according to example embodiments.

The body 110 may be formed with a nonconductive material. As illustrated in FIG. 1A, the body 100 may include a plurality of recessed regions 160 that are formed at locations corresponding to vertexes of N-polygon, where N is an even number. In example embodiments, the nonconductive material may include nonconductive rubber. However, the nonconductive material is not limited to the nonconductive rubber. For example, the nonconductive material may be various nonconductive materials having elasticity. In an example embodiment, the body 110 may have a cylinder shape. It is illustrated in FIG. 1A that the body 110 has the cylinder shape. Thus, a shape of the shoe insole sensor 100 may be a circle shape from a top view of the shoe insole sensor 100. In FIG. 1A, it is illustrated that the recessed regions 160 that are formed in the body 110 have a cylinder shape, respectively. Hence, the first and second protrusions 120 and 140 that are formed in the recessed regions 160 may have a cylinder shape, respectively.

In addition, since the recessed regions 160 are formed at locations corresponding to the vertexes of the N-polygon in the body 110, the shoe insole sensor 100 may achieve high sensing accuracy regardless of directions in which a pressure is applied to the shoe insole sensor 100. Specifically, the N-polygon may be 4-polygon (i.e., tetragon), 6-polygon (i.e., hexagon), 8-polygon (i.e., octagon), 10-polygon (i.e., decagon), 12-polygon (i.e., dodecagon), etc. However, when the N-polygon is determined to be the 4-polygon, the sensing accuracy of the shoe insole sensor 100 may be degraded. In addition, when the N-polygon is determined to be the 8-polygon, the 10-polygon, the 12-polygon, etc, the sensing accuracy of the shoe insole sensor 100 may not be improved compared to when the N-polygon is determined to be the 6-polygon. Therefore, it is desirable to determine the N-polygon to be the 6-polygon because performance per price of the shoe insole sensor 100 is better when the N-polygon is determined to be the 6-polygon. However, it should be understood that an arrangement of the recessed regions 160 that are formed in the body 110 is not limited to a 6-polygon shape. In addition, sensing sensitivity of the shoe insole sensor 100 may be influenced by a property of the nonconductive material (e.g., the nonconductive rubber, etc) of the body 110, an entire volume of concave regions 170 and 180 included in the body 110, etc. Thus, when manufacturing the shoe insole sensor 100, the sensing sensitivity of the shoe insole sensor 100 may be adjusted by adjusting the property of the nonconductive material of the body 110, the entire volume of the concave regions 170 and 180 included in the body 110, etc. Although it is described above that the recessed regions 160 are formed at locations corresponding to the vertexes of the N-polygon in the body 110, it should be understood that the recessed regions 160 may be formed at locations corresponding to sides of the N-polygon in the body 110.

In addition, each of the first and second protrusions 120 and 140 may be formed with a conductive material. In example embodiments, the conductive material may include conductive rubber. However, the conductive material is not limited to the conductive rubber. For example, the conductive material may be various conductive materials having flexibility. As illustrated in FIG. 1A, each of the first protrusions 120 may have a first height and may be formed in odd recessed regions 160 of the recessed regions 160 of the body 110. In addition, each of the second protrusions 140 may have a second height that is different from the first height and may be formed in even recessed regions 160 of the recessed regions 160 of the body 110. Here, "odd" and "even" do not have any important meanings in the present inventive concept because the odd recessed regions 160 and the even recessed regions 160 are determined according to how a reference point is set to distinguish the odd recessed regions 160 from the even recessed regions 160. In other words, "odd" and "even" indicate that the first protrusions 120 and the second protrusions 140 are alternately formed in the recessed regions 160 of the body 110 in a clockwise direction or in a counter clockwise direction. In addition, the first protrusions 120 and the second protrusions 140 that are adjacent to each other may act as respective sensing pairs. That is, one first protrusion 120 and one second protrusion 140 that are adjacent to each other may act as a sensing pair. Here, respective sensing pairs may implement data resolution based on the first height of the first protrusions 120 and the second height of the second protrusions 140. Although it is illustrated in FIG. 1B that the first height of the first protrusions 120 is lower than the second height of the second protrusions 140, the first height of the first protrusions 120 may be higher than the second height of the second protrusions 140.

The shoe insole sensor 100 may be disposed on a shoe insole flexible board. Thus, when a pressure is applied to the shoe insole sensor 100 (i.e., from above), the shoe insole sensor 100 may be pressurized on the shoe insole flexible board. As a result, a sensing operation may be performed because the first protrusions 120 and the second protrusions 140 of the shoe insole sensor 100 may be contacted with a plurality of switches included in the shoe insole flexible board. That is, since the first protrusions 120 and the second protrusions 140 of the shoe insole sensor 100 are formed with the conductive material, the first protrusions 120 and the second protrusions 140 can turn-on the switches included in the shoe insole flexible board. Specifically, the first and second protrusions 120 and 140 of the shoe insole sensor 100 may be disposed on locations corresponding to the switches included in the shoe insole flexible board. In addition, a switch of the shoe insole flexible board may be turned-on when the switch is contacted with a corresponding protrusion (i.e., the first and second protrusions 120 and 140) as a pressure is applied to the shoe insole sensor 100. Here, since the first height of the first protrusions 120 is different from the second height of the second protrusions 140, only the second protrusions 140 may be contacted with the switches of the shoe insole flexible board when a relatively weak pressure is applied to the shoe insole sensor 100. In addition, both the first protrusions 120 and the second protrusions 140 may be contacted with the switches of the shoe insole flexible board when a relatively strong pressure is applied to the shoe insole sensor 100. On this basis (i.e., based on the above switching operation), the shoe insole sensor 100 combined with the shoe insole flexible board may implement data resolution having three levels (e.g., a zero ('off'-'off') level, a weak ('off'-'on') level, a strong level ('on'-'on') level). In some example embodiments, when first protrusions having a first height, second protrusions having a second height that is different from the first height, and third protrusions having a third height that is different from the first and second heights exist, the shoe insole sensor 100 combined with the shoe insole flexible board may implement data resolution having four levels (e.g., a zero ('off'-'off'-'off') level, a first weak ('off'-'off'-'on') level, a second weak ('off'-'on'-'on') level, and a strong level ('on'-'on'-'on') level). Here, the sensing sensitivity of the shoe insole sensor 100 may further be influenced by the first height of the first protrusions 120, the second height of the second protrusions 140, a property of the conductive material (e.g., the conductive rubber, etc) of the first and second protrusions 120 and 140, etc. Thus, the sensing sensitivity of the shoe insole sensor 100 may further be adjusted by adjusting the first height of the first protrusions 120, the second height of the second protrusions 140, the property of the conductive material of the first and second protrusions 120 and 140, etc.

As described above, in the shoe insole sensor 100, the first protrusions 120 and the second protrusions 140 that are adjacent to each other may act as respective sensing pairs, and respective sensing pairs may implement data resolution based on the first height of the first protrusions 120 and the second height of the second protrusions 140. As illustrated in FIG. 1B, one first protrusion 120 and one second protrusion 140 that are formed in adjacent recessed regions 160 of the body 110 may act as a sensing pair, and the sensing pair may implement data resolution having three levels. That is, the sensing pair provides sensing data indicating that no pressure is applied to the shoe insole sensor 100 (i.e., the zero level), that a relatively weak pressure is applied to the shoe insole sensor 100 (i.e., the weak level), or that a relatively strong pressure is applied to the shoe insole sensor 100 (i.e., the strong level). Generally, because of a foot shape and/or walking posture of a person (i.e., walker), a pressure may not be applied to the shoe insole sensor 100 in a perpendicular direction to the shoe insole sensor 100. That is, a pressure may be applied to the shoe insole sensor 100 in a slanted direction with respect to a normal of the shoe insole sensor 100 when the person steps on the shoe insole sensor 100. However, the shoe insole sensor 100 may achieve high sensing accuracy regardless of directions in which a pressure is applied to the shoe insole sensor 100 because the first protrusions 120 and the second protrusions 140 that are adjacent to each other act as respective sensing pairs. For example, as illustrated in FIG. 1A, six recessed regions 160 may be formed at six locations corresponding to six vertexes of 6-polygon in the body 110, and three first protrusions 120 and three second protrusions 140 may be alternately formed in the six recessed regions 160. In this case, when a pressure is applied to the shoe insole sensor 100 in any direction intersecting with six sides of the 6-polygon, a sensing pair (i.e., one first protrusion 120 and one second protrusion 140) related to the direction may sense the pressure, so that the shoe insole sensor 100 may achieve high sensing accuracy regardless of directions in which a pressure is applied to the shoe insole sensor 100.

In brief, the shoe insole sensor 100 may accurately detect a pressure using the first protrusions 120 and the second protrusions 140 that act as respective sensing pairs when the pressure is applied to the shoe insole sensor 100 in a slanted direction with respect to a normal of the shoe insole sensor 100. In addition, the shoe insole sensor 100 may further provide high data resolution based on a difference between the first height of the first protrusions 120 and the second height of the second protrusions 140. Further, since the sensing data is generated by turning-on or turning-off the switches of the shoe insole flexible board based on whether the first protrusions 120 and the second protrusions 140 of the shoe insole sensor 100 are contacted with the switches of the shoe insole flexible board, the shoe insole sensor 100 may consume lower power, may have a smaller size, and may be manufactured at lower cost compared to a conventional high performance sensor. As a result, a walk diagnosis system employing the shoe insole sensor 100 may extract walking data during a long time in real life of a person by encouraging the person just to wear a pair of shoes that includes a shoe insole in which the shoe insole sensor 100 is disposed on the shoe insole flexible board. That is, compared to a conventional walk diagnosis system that extracts walking data during a limited time in a specific facility (e.g., a hospital, a health examination center, etc), the walk diagnosis system employing the shoe insole sensor 100 may obtain sufficient walking data enough to accurately analyze walking posture of the person. In particular, since the shoe insole sensor 100 can be manufactured at low cost, a walk diagnosis service (e.g., health checking service based on walk diagnosis) provided by the walk diagnosis system employing the shoe insole sensor 100 may be promoted (or, activated) owing to its cheapness and convenience. That is, the present inventive concept may enable the walk diagnosis service to become popular and common in the near future. In some example embodiments, the shoe insole sensor (i.e., pressure detection sensor) 100 may be used for other products (e.g., a chair, a bed, etc).

Figure 2:
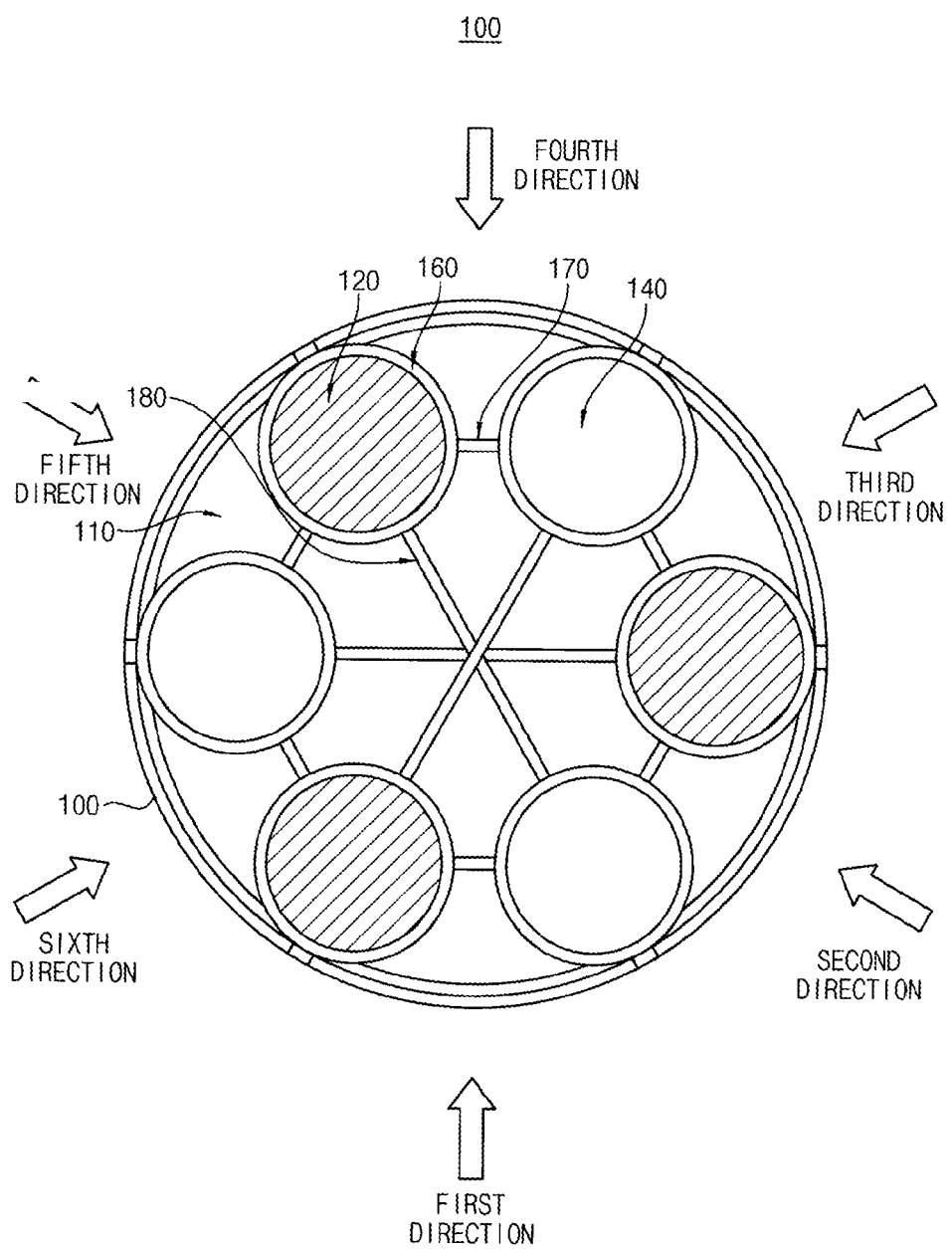
FIGS. 2 and 3 are diagrams for describing sensing accuracy according to directions in which a pressure is applied to the shoe insole sensor of FIG. 1A.
Figure 3:
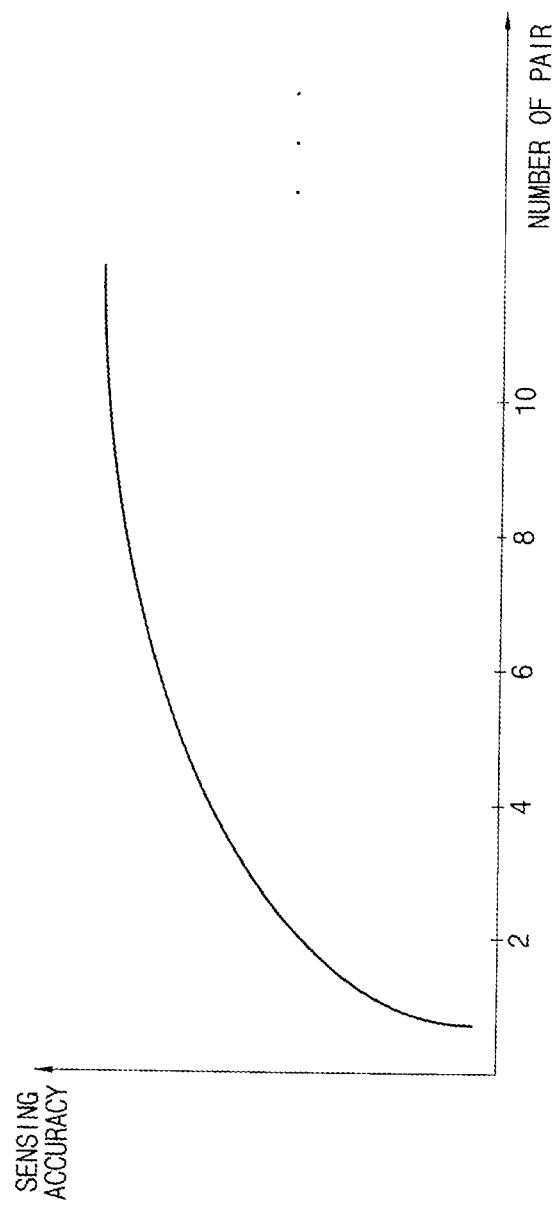

FIGS. 2 and 3 are diagrams for describing sensing accuracy according to directions in which a pressure is applied to the shoe insole sensor of FIG. 1A.

Referring to FIGS. 2 and 3, FIG. 2 shows that the first protrusions 120 and the second protrusions 140 act as respective sensing pairs in the shoe insole sensor 100. In addition, FIG. 3 shows sensing accuracy according to a quantity of the sensing pairs in the shoe insole sensor 100.

In example embodiments, when the recessed regions 160 are formed at locations corresponding to vertexes of N-polygon, where N is an even number, in the body 110 and when the first protrusions 120 and the second protrusions 140 are alternately formed in the recessed regions 160, the quantity of the sensing pairs each including one first protrusion 120 and one second protrusion 140 may be N in the shoe insole sensor 100. As illustrated in FIG. 2, when six recessed regions 160 are formed at six locations corresponding to six vertexes of 6-polygon in the body 110 and when three first protrusions 120 and three second protrusions 140 are alternately formed in the six recessed regions 160, the quantity of the sensing pairs each including one first protrusion 120 and one second protrusion 140 may be 6 in the shoe insole sensor 100. In FIG. 2, six arrows indicate six slanted directions FIRST DIRECTION, SECOND DIRECTION, THIRD DIRECTION, FOURTH DIRECTION, FIFTH DIRECTION, and SIXTH DIRECTION, respectively in which a pressure is applied to the shoe insole sensor 100. Thus, six sensing pairs may react to the six arrows.

As described above, because of a foot shape and/or walking posture of a person, a pressure may not be applied to the shoe insole sensor 100 in a perpendicular direction to the shoe insole sensor 100. That is, a pressure may be applied to the shoe insole sensor 100 in a slanted direction with respect to a normal of the shoe insole sensor 100 when the person steps on the shoe insole sensor 100. For example, as illustrated in FIG. 2, a pressure may be applied to the shoe insole sensor 100 in various directions (e.g., in the six slanted directions indicated as the six arrows) from a top view of the shoe insole sensor 100. However, the shoe insole sensor 100 may achieve high sensing accuracy regardless of directions in which a pressure is applied to the shoe insole sensor 100 because the first protrusions 120 and the second protrusions 140 that are adjacent to each other act as respective sensing pairs. Here, as the quantity of the sensing pairs (i.e., N) each including one first protrusion 120 and one second protrusion 140 increases, the shoe insole sensor 100 may more accurately react to a pressure that is applied to the shoe insole sensor 100 in various directions. That is, as a quantity of the first protrusions 120 and a quantity of the second protrusions 140 increase, the shoe insole sensor 100 may more accurately react to a pressure that is applied to the shoe insole sensor 100 in various directions.

For example, when a plurality of recessed regions (i.e., twelve recessed regions) 160 are formed at twelve locations corresponding to twelve vertexes of 12-polygon in the body 110 and when six first protrusions 120 and six second protrusions 140 are alternately formed in the twelve recessed regions 160, the quantity of the sensing pairs each including one first protrusion 120 and one second protrusion 140 may be 12 in the shoe insole sensor 100. In this case, since the shoe insole sensor 100 including twelve sensing pairs reacts to a pressure that is applied to the shoe insole sensor 100 in more subdivided directions (e.g., twelve slanted directions), the shoe insole sensor 100 including twelve sensing pairs may achieve higher sensing accuracy compared to the shoe insole sensor 100 of FIG. 2 including six sensing pairs. Here, increasing the quantity of the recessed regions 160 that are formed in the body 100, the quantity of the first protrusions 120, and the quantity of the second protrusions 140 may result in increasing power consumption, increasing a size of the shoe insole sensor 100, increasing manufacturing cost, etc. As illustrated in FIG. 3, when N is greater than or equal to 8, sensing accuracy of the shoe insole sensor 100 may be improved very little compared to when N is 6. That is, when N is greater than or equal to 8, the sensing accuracy of the shoe insole sensor 100 may be saturated (or, converged) to a specific value as N increases. Therefore, it is desirable to determine N to be 6 because performance per price of the shoe insole sensor 100 is better when N is determined to be 6. However, an arrangement of the recessed regions 160 that are formed in the body 110 is not limited to the 6-polygon shape illustrated in FIG. 2.

Figure 4:
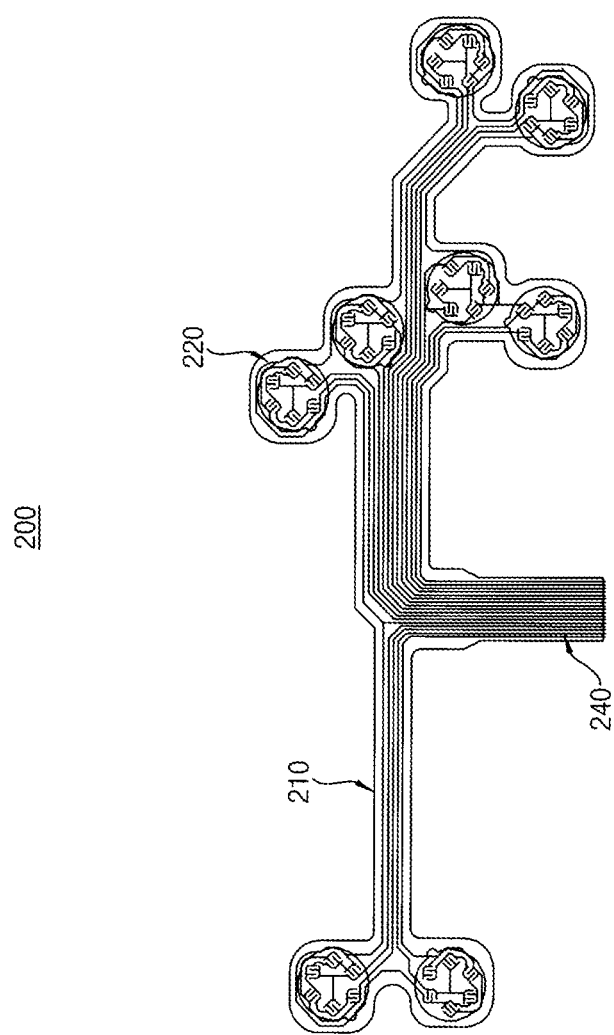
FIG. 4 is a diagram illustrating a shoe insole flexible board according to example embodiments.

FIG. 4 is a diagram illustrating a shoe insole flexible board according to example embodiments.

Referring to FIG. 4, the shoe insole flexible board (i.e., pressure detection flexible board) 200 may include a plurality of switching units 220 and a plurality of wiring units 240. Here, the wiring units 240 may be connected to the switching units, respectively. In an example embodiment, the shoe insole flexible board 200 may be manufactured by printing the switching units 220 and the wiring units 240 on a board 210. In this case, manufacturing cost of the shoe insole flexible board 200 may be reduced. For example, the board 210 may include a flexible board, a film, etc on which the switching units 220 and the wiring units 240 are formed by a printing technique, a coating technique, a copying technique, an etching technique, etc.

Each of the switching units 220 may include N switches that are formed at locations corresponding to vertexes of N-polygon, where N is an even number. Here, adjacent two switches of the N switches may act as a sensing pair. For example, as illustrated in FIG. 4, each of the switching units 220 may include six switches of which adjacent two switches act as a sensing pair. Each of the wiring units 240 may include a voltage supply line that provides a reference voltage, a first wiring that transfers a first sensing signal, and a second wiring that transfers a second sensing signal. Here, the voltage supply line may be connected to the N switches, the first wiring may be connected to first switches (e.g. odd switches) of the N switches, and the second wiring is connected to second switches (e.g., even switches) of the N switches. Thus, each of the wiring units 240 may include three wirings, and each of the switching units 220 may be connected to each of the wiring units 240, namely, the three wirings. For example, as illustrated in FIG. 4, eight switching units 220 may be connected to eight wiring units 240, respectively. Here, the voltage supply line may be shared. On this basis, the shoe insole flexible board 200 may output sensing data based on the first and second sensing signals that are generated by contact-operations with a plurality of shoe insole sensors. As a result, the shoe insole flexible board 200 combined with the shoe insole sensors may implement data resolution having three levels.

Specifically, data resolution may be determined based on whether the first sensing signal and the second sensing signal are generated, respectively. Here, the first sensing signal may be generated when a reference voltage is applied to the first wiring as at least one of the first switches is turned-on. The second sensing signal may be generated when the reference voltage is applied to the second wiring as at least one of the second switches is turned-on. As described above, each of the shoe insole sensors that are disposed on the shoe insole flexible board 200 may include a plurality of first protrusions having a first height and a plurality of second protrusions having a second height that is different from the first height. Here, since the first protrusions and the second protrusions have different heights, a pressure that can turn-on the first switches of the shoe insole flexible board 200 may be different from a pressure that can turn-on the second switches of the shoe insole flexible board 200. Thus, when a relatively weak pressure is applied to the shoe insole sensors combined with the shoe insole flexible board 200 (i.e., from above), one of the first sensing signal and the second sensing signal may be generated. In addition, when a relatively strong pressure is applied to the shoe insole sensors combined with the shoe insole flexible board 200, both of the first sensing signal and the second sensing signal may be generated. As a result, it may be determined that a relatively weak pressure is applied to the shoe insole sensors combined with the shoe insole flexible board 200 when one of the first sensing signal and the second sensing signal is generated. In addition, it may be determined that a relatively strong pressure is applied to the shoe insole sensors combined with the shoe insole flexible board 200 when both of the first sensing signal and the second sensing signal are generated. Further, it may be determined that no pressure is applied to the shoe insole sensors combined with the shoe insole flexible board 200 when none of the first sensing signal and the second sensing signal are generated. In other words, the shoe insole flexible board 200 combined with the shoe insole sensors may implement data resolution having a plurality of levels (e.g., three levels).

Figure 5:
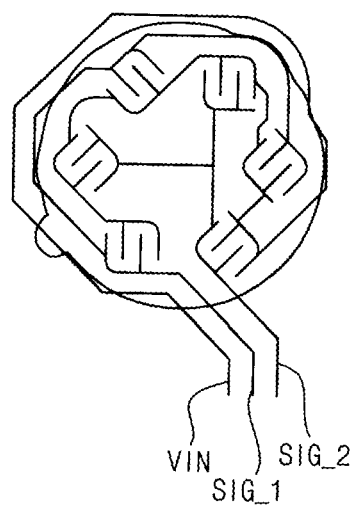
FIG. 5 is a diagram illustrating a switching unit included in the shoe insole flexible board of FIG. 4.
Figure 6:
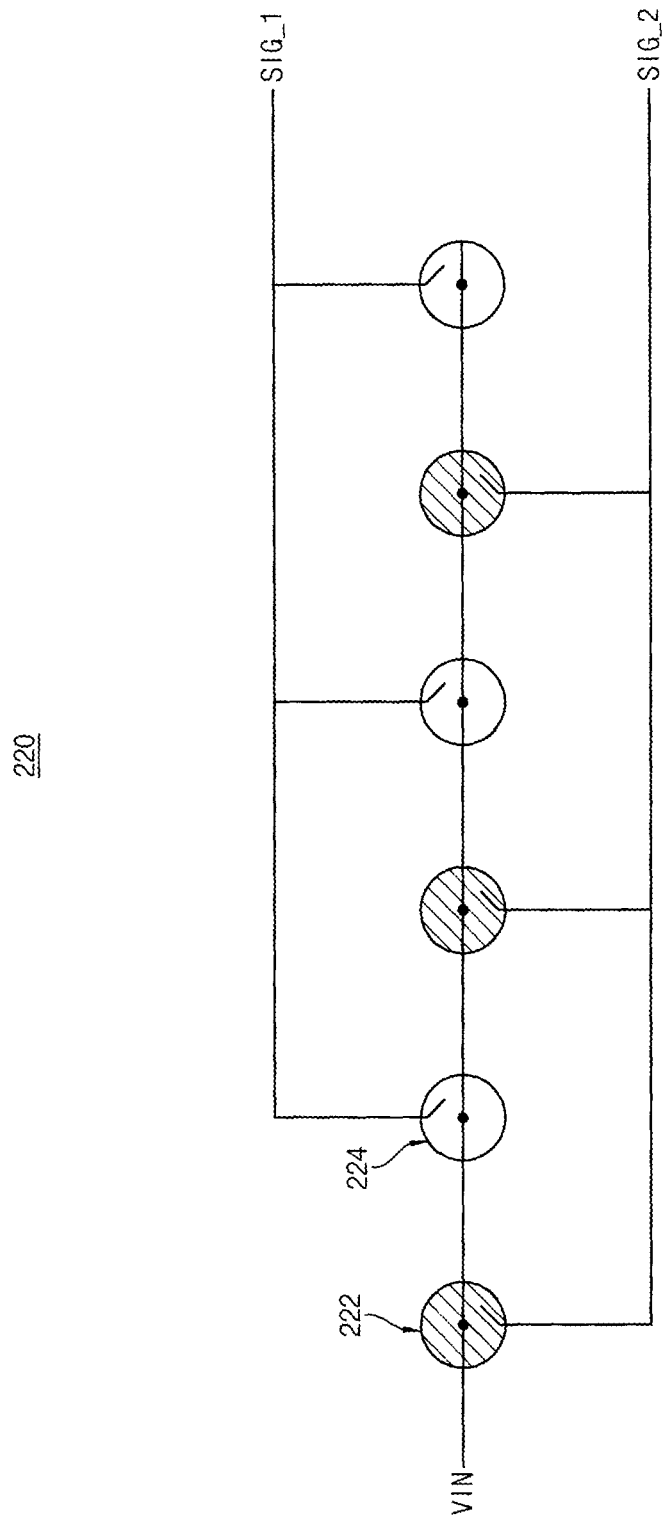
FIG. 6 is a diagram for describing an operation of the switching unit of FIG. 5.

FIG. 5 is a diagram illustrating a switching unit included in the shoe insole flexible board of FIG. 4. FIG. 6 is a diagram for describing an operation of the switching unit of FIG. 5.

Referring to FIGS. 5 and 6, each of the switching units 220 may include N switches at locations corresponding to vertexes of N-polygon, where N is an even number, and adjacent two switches of the N switches may act as a sensing pair. For example, as illustrated in FIG. 5, each of the switching units 220 may include six switches 222 and 224 of which adjacent two switches 222 and 224 act as a sensing pair. That is, six sensing pairs may exist in each of the switching units 220.

Each of the switching units 220 may be connected to each of the wirings 240 including the voltage supply line that provides a reference voltage VIN, a first wiring that transfers a first sensing signal SIG-1, and a second wiring that transfers a second sensing signal SIG-2. FIG. 6 shows detailed connections of the six switches 222 and 224 included in each of the switching units 220. As illustrated in FIGS. 5 and 6, while the reference voltage VIN is applied via the voltage supply line, the first sensing signal SIG-1 and/or the second sensing signal SIG-2 may be generated based on whether the six switches 222 and 224 turn-on or turn-off. Here, the voltage supply line may be connected to the six switches 222 and 224, the first wiring may be connected to the first switches 224 (e.g., even switches) of the six switches 222 and 224, and the second wiring may be connected to the second switches 222 (e.g., odd switches) of the six switches 222 and 224. As a result, the first sensing signal SIG-1 may be output when at least one switch of the first switches 224 turns-on, and the second sensing signal SIG-2 may be output when at least one switch of the second switches 222 turns-on. As described above, since one first switch 224 and one second switch 222 that are adjacent to each other act as a sensing pair related to any direction intersecting with sides of the N-polygon, each of the switching units 220 included in the shoe insole flexible board 200 may achieve high sensing accuracy regardless of directions in which a pressure is applied to each of the switching units 220 included in the shoe insole flexible board 200. For example, assuming that N is 6 as illustrated in FIG. 5, a first odd switch 224 and a first even switch 222 may act as a first sensing pair, the first even switch 222 and a second odd switch 224 may act as a second sensing pair, the second odd switch 224 and a second even switch 222 may act as a third sensing pair, the second even switch 222 and a third odd switch 224 may act as a fourth sensing pair, the third odd switch 224 and a third even switch 222 may act as a fifth sensing pair, and the third even switch 222 and the first odd switch 224 may act as a sixth sensing pair (i.e., the third even switch 222 and the first odd switch 224 are adjacent to each other because the switches 222 and 224 are arranged in a circle shape). Thus, the shoe insole flexible board 200 may output sensing data based on the first and second sensing signals SIG-1 and SIG-2 that are generated by contact-operations with the shoe insole sensors. As a result, the shoe insole flexible board 200 combined with the shoe insole sensors may implement data resolution having a plurality of levels (e.g., three levels).

Figure 7:
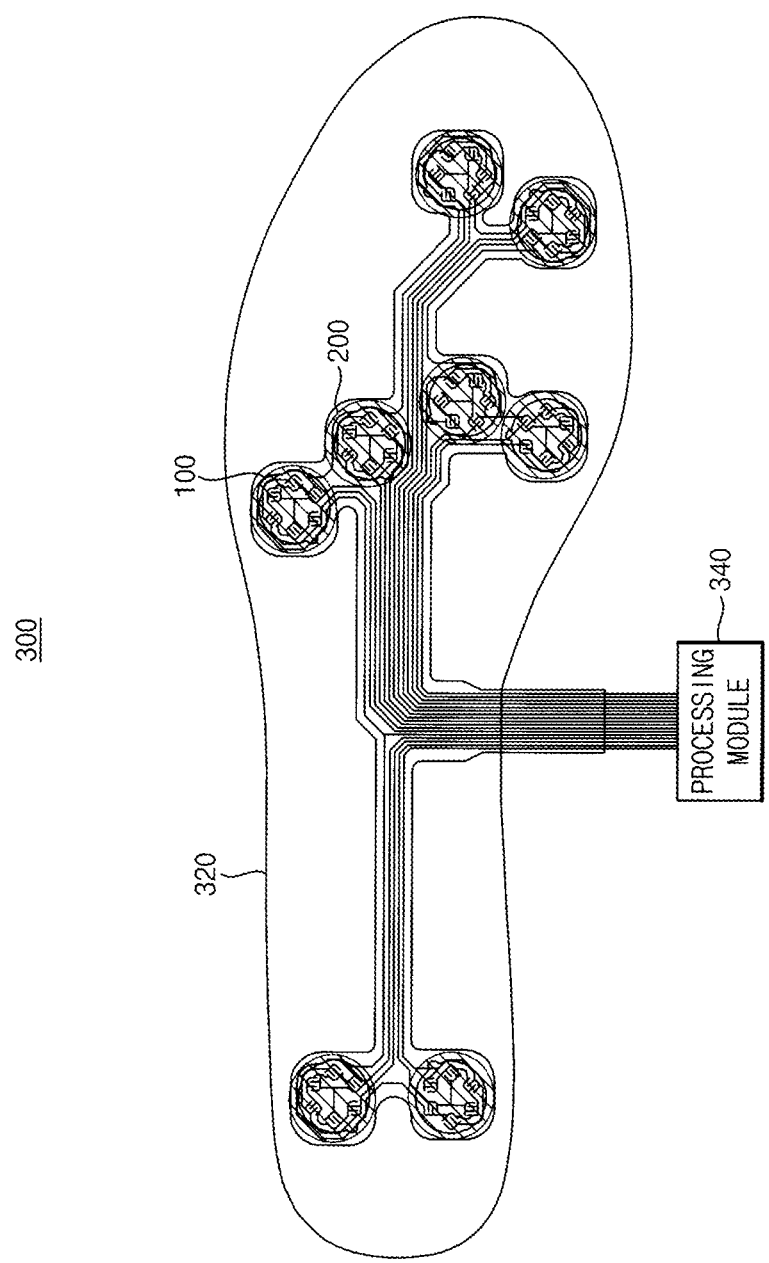
FIG. 7 is a diagram illustrating a shoe insole according to example embodiments.
Figure 8:
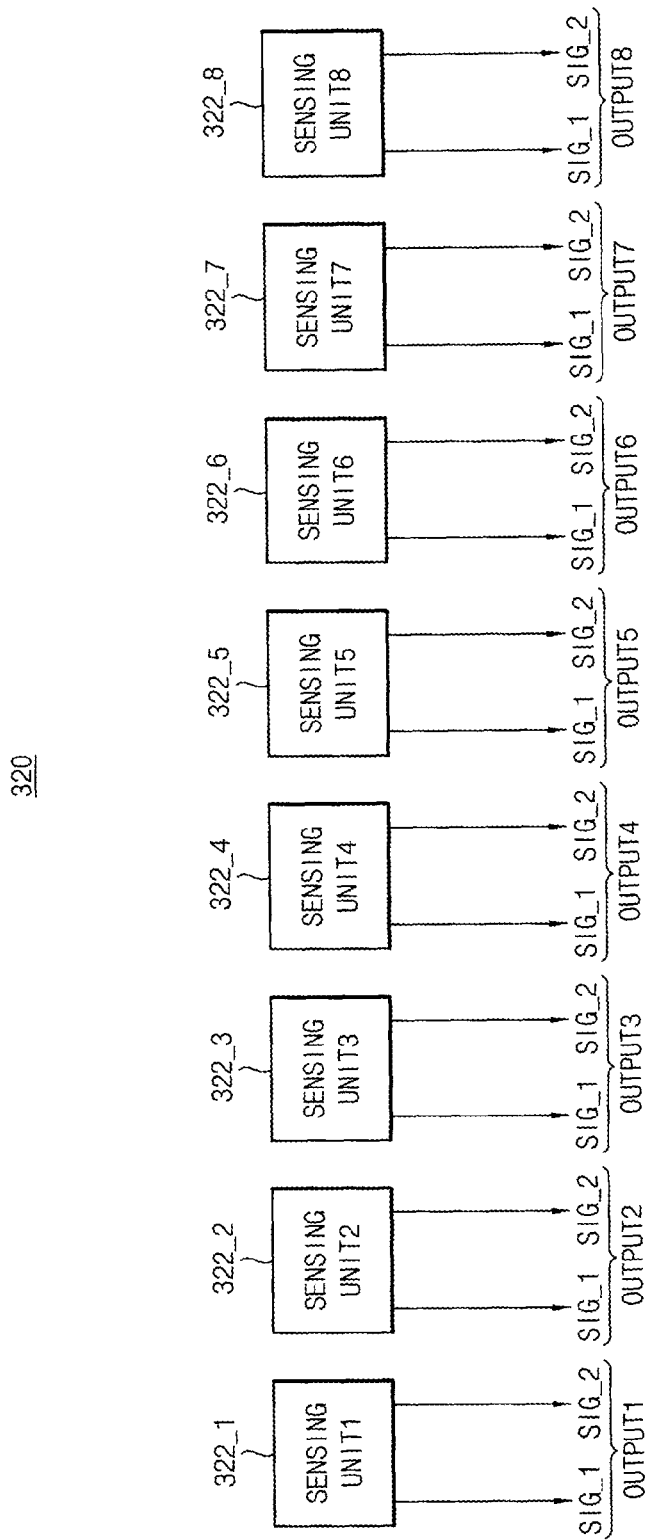
FIG. 8 is a block diagram illustrating a plurality of sensing units included in the shoe insole of FIG. 7.
Figure 9:
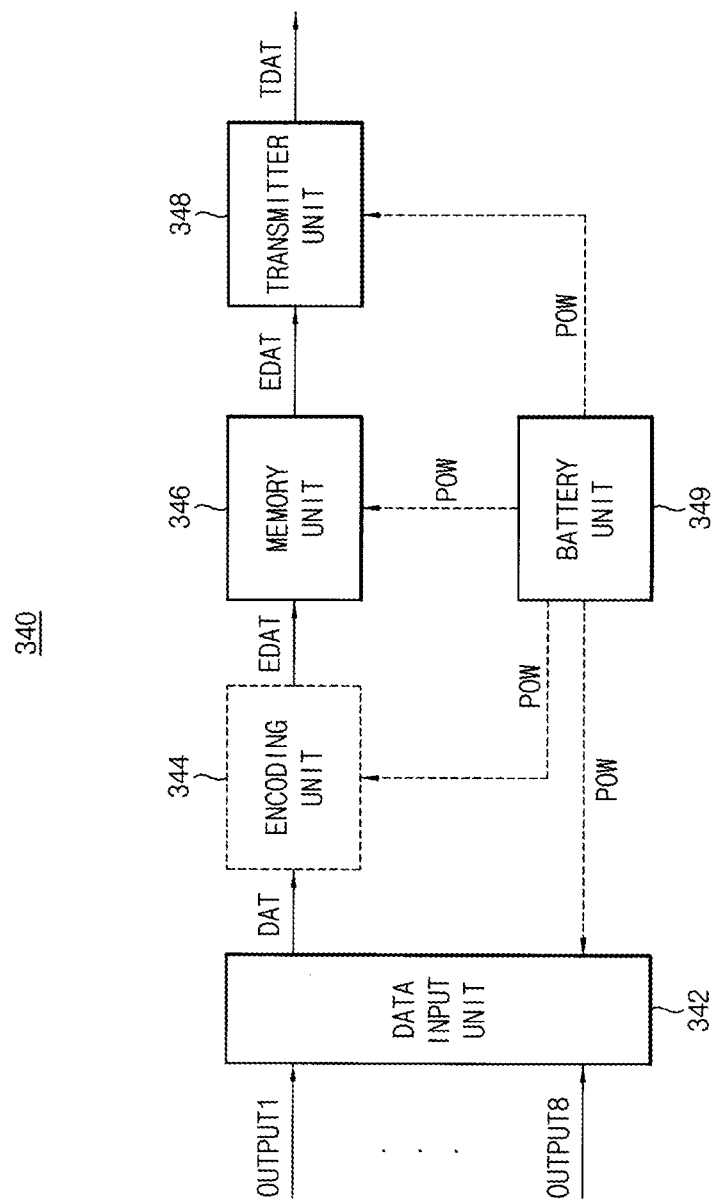
FIG. 9 is a block diagram illustrating a processing module included in the shoe insole of FIG. 7.

FIG. 7 is a diagram illustrating a shoe insole according to example embodiments. FIG. 8 is a block diagram illustrating a plurality of sensing units included in the shoe insole of FIG. 7. FIG. 9 is a block diagram illustrating a processing module included in the shoe insole of FIG. 7.

Referring to FIGS. 7 through 9, the shoe insole 300 may include a sensor unit 320 and a processing module 340. Here, the sensor unit 320 may include at least one shoe insole sensor 100 and a shoe insole flexible board 200. Since the shoe insole sensor 100 and the shoe insole flexible board 200 are described above, duplicated description will not be repeated. In some example embodiments, the shoe insole 300 may further include a plurality of sensors such as a gyroscope sensor, an acceleration sensor, a temperature sensor, a humidity sensor, a global positioning system (GPS), a geomagnetic sensor, etc.

The sensor unit 320 may include first through eighth sensing units 322-1 through 322-8. Each of the first through eighth sensing units 322-1 through 322-8 may correspond to a combination of the shoe insole sensor 100 and the shoe insole flexible board 200. That is, the sensor unit 320 may have a structure in which eight shoe insole sensors 100 are disposed on the shoe insole flexible board 200. However, a quantity of the shoe insole sensors 100 combined with the shoe insole flexible board 200 is not limited thereto. Thus, the quantity of the shoe insole sensors 100 combined with the shoe insole flexible board 200 may be determined according to requirements for a walk diagnosis system. As described above, the shoe insole sensor 100 combined with the shoe insole flexible board 200 may implement data resolution having a plurality of levels (e.g., three levels). Thus, each of the first through eighth sensing units 322-1 through 322-8 may generate and output the first sensing signal SIG-1 and/or the second sensing signal SIG-2. For example, assuming that an output OUTPUT1 of the first sensing unit 322-1 includes the first sensing signal SIG-1 and the second sensing signal SIG-2, respective outputs OUTPUT2 through OUTPUT7 of the second through seventh sensing units 322-2 through 322-7 include one of the first sensing signal SIG-1 and the second sensing signal SIG-2, and an output OUTPUT8 of the eighth sensing unit 322-8 includes none of the first sensing signal SIG-1 and the second sensing signal SIG-2, it may be determined that a relatively strong pressure is applied to the first sensing unit 322-1, that a relatively weak pressure is applied to the second through seventh sensing units 322-2 through 322-7, and that no pressure is applied to the eighth sensing unit 322-8. As described above, the outputs OUTPUT1 through OUTPUT8 of the sensor unit 320 may include information related to magnitude/location of the pressure that is applied to the shoe insole 300 from above.

The processing module 340 may include a data input unit 342, an encoding unit 344, a memory unit 346, a transmitter unit 348, and a battery unit 349. Specifically, the data input unit 342 may receive the outputs OUTPUT1 through OUTPUT8 of the sensor unit 320 and may output the outputs OUTPUT1 through OUTPUT8 of the sensor unit 320 as sensing data DAT. The encoding unit 344 may receive the sensing data DAT and may encode the sensing data DAT in a predetermined format to generate encoded sensing data EDAT. Here, since the sensing data DAT is encoded in the predetermined format by the encoding unit 344, the sensing data DAT may be efficiently stored in the memory unit 346. That is, the encoded sensing data EDAT may be stored in the memory unit 346. Thus, power consumption may be reduced. For this reason, it is desirable for the processing module 340 to include the encoding unit 344. However, the encoding unit 344 may not be included in the processing module 340. The memory unit 346 may store the encoded sensing data EDAT and may output the encoded sensing data EDAT as walking data TDAT via the transmitter unit 348 at a predetermined timing. For example, the memory unit 346 may output the encoded sensing data EDAT as the walking data TDAT via the transmitter unit 348 while the battery unit 349 is charged. The battery unit 349 may supply the sensor unit 320 and the processing module 340 with required power. In example embodiments, the battery unit 349 may be wirelessly charged by a wireless charger. In addition, the transmitter unit 348 may provide the walking data TDAT to an external system (e.g., a central server that is external to the shoe insole 300, etc) using various wire and/or wireless communication technologies.

Figure 10:
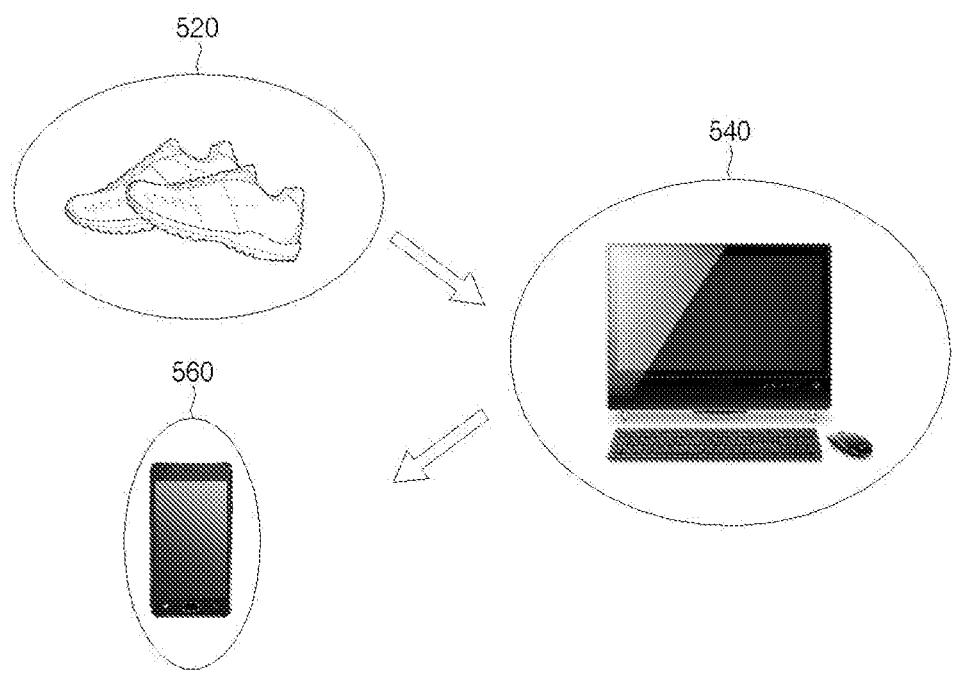
FIG. 10 is a diagram illustrating a walk diagnosis system according to example embodiments.

FIG. 10 is a diagram illustrating a walk diagnosis system according to example embodiments.

Referring to FIG. 10, the walk diagnosis system 500 may include a pair of shoes 520 each having a shoe insole 300 according to example embodiments, a central server 540, and a user device 560. Since the shoe insole 300 according to example embodiments is described above, duplicated description will not be repeated.

The pair of shoes 520 may extract walking data during a long time in real life of a person (i.e., walker) that uses a walk diagnosis service (e.g., health checking service based on walk diagnosis). That is, the person is just required to wear the pair of shoes 520 in order to use the walk diagnosis system. Since a conventional shoe insole mostly focuses on high performance by using expensive sensors, the conventional shoe insole may be very expensive and may consume high power. In addition, a person wearing a pair of shoes each having the conventional shoe insole may be required to wear an additional device such as a wristwatch, a smart phone, etc for communicating with the conventional shoe insole to receive walking data from the conventional shoe insole. Thus, conventionally, extracting the walking data is generally performed during a limited time in a specific facility such as a hospital, a health examination center, etc. For this reason, it has been difficult to enable the walk diagnosis service to become popular and common. Further, it has been difficult to accurately analyze walking posture of the person based on the walking data that are extracted in a limited time in a specific facility such as a hospital, a health examination center, etc. On the other hand, since the shoe insole 300 included in the pair of shoes 520 includes the shoe insole sensor 100 and the shoe insole flexible board 200 that can be manufactured at low cost, the walk diagnosis system 500 may enable the person to inexpensively and conveniently use the health checking service based on walk diagnosis. In addition, in the walk diagnosis system 500, the person wearing the pair of shoes 520 may not be required to wear an additional device such as a wristwatch, a smart phone, etc for communicating with the shoe insole 300. As a result, convenience for using the health checking service based on walk diagnosis may be maximized.

The central server 540 may store the walking data that are provided (or, transmitted) from the pair of shoes 520, and may analyze the walking data by using an analysis system or an experts group (e.g., doctor, physical education professional, rehabilitation professional, posture correction professional, walking analysis professional, psychological analysis professional, image making professional, etc). As a result, walk diagnosis data may be generated based on the walking data, and the walk diagnosis data may be provided to a person that uses the health checking service based on walk diagnosis. In some example embodiments, since the central server 540 receives and stores the walking data of many persons, the central server 540 may perform encryption/decryption for performing a personal privacy protection. The user device 560 may receive the walk diagnosis data from the central server 540. Here, the user device 560 may correspond to a personal computer (PC), a laptop, a cellular phone, a smart phone, a smart pad, a tablet PC, etc. Thus, the user device 560 may enable the person that uses the health checking service based on walk diagnosis to check his walk diagnosis (e.g., a warning of falling, a notice of amount of exercise, a notice of amount of action for old people, a notice of exercise prescription, etc). In brief, the walk diagnosis system 500 may extract the walking data during a long time in real life of the person that uses the walk diagnosis service, where the person is just required to wear the pair of shoes 520. Therefore, compared to the conventional walk diagnosis system that extracts the walking data during a limited time in a specific facility such as a hospital, a health examination center, etc, the walk diagnosis system 500 may obtain sufficient walking data enough to accurately analyze walking posture of the person. As a result, the present inventive concept may enable the walk diagnosis service (e.g., health checking service based on walk diagnosis) to become popular and common in the near future.

Although a few example embodiments (e.g., a shoe insole sensor, a shoe insole flexible board, a shoe insole, and a walk diagnosis system) have been described, those skilled in the art will readily appreciate that many modifications are possible in the example embodiments without materially departing from the novel teachings and advantages of the present inventive concept. Thus, structures of the shoe insole sensor, the shoe insole flexible board, the shoe insole, and the walk diagnosis system are not limited to the above-described example embodiments.

The present inventive concept may be applied to a shoe insole for walk diagnosis. Thus, the present inventive concept may be applied to a walk diagnosis system in which waking data of a human is extracted by a shoe insole for walk diagnosis included in a shoe that the human wears, and walk diagnosis is performed based on the walking data.

The foregoing is illustrative of example embodiments and is not to be construed as limiting thereof Although a few example embodiments have been described, those skilled in the art will readily appreciate that many modifications are possible in the example embodiments without materially departing from the novel teachings and advantages of the present inventive concept. Accordingly, all such modifications are intended to be included within the scope of the present inventive concept as defined in the claims. Therefore, it is to be understood that the foregoing is illustrative of various example embodiments and is not to be construed as limited to the specific example embodiments disclosed, and that modifications to the disclosed example embodiments, as well as other example embodiments, are intended to be included within the scope of the appended claims.

What is claimed is:

1. A shoe insole sensor comprising:
    a body including a plurality of recessed regions formed at respective locations corresponding to vertexes of N-polygon, where N is an even number greater than 2, the body being formed with a nonconductive material;
    a plurality of first protrusions formed in odd recessed regions of the recessed regions, each of the first protrusions having a first height, each of the first protrusions being formed with a conductive material; and
    a plurality of second protrusions formed in even recessed regions of the recessed regions, each of the second protrusions having a second height different from the first height, each of the second protrusions being formed with a conductive material,
    wherein the first protrusions and the second protrusions that are adjacent to each other act as respective sensing pairs, and the sensing pairs implement data resolution based on the first height and the second height.

2. The sensor of claim 1, wherein the body has a cylinder shape.

3. The sensor of claim 1, wherein each of the recessed regions has a cylinder shape, each of the first protrusions has the cylinder shape, and each of the second protrusions has the cylinder shape.

4. The sensor of claim 1, wherein the conductive material includes conductive rubber and the nonconductive material includes nonconductive rubber.

\* \* \* \* \*